(12) United States Patent
Callan (10) Patent No.: US 8,485,819 B2
(45) Date of Patent: Jul. 16, 2013

(54) DENTAL IMPLANT (75) Inventor: Donald P. Callan, Little Rock, AR (US)

(73) Assignee: Perioseal, Inc., Little Rock, AR (US)

( * ) Notice: Subject to any disclaimer, the term of this patent is extended or adjusted under 35 U.S.C. 154(b) by 0 days.

(21) Appl. No.: 13/198,444

(22) Filed: Aug. 4, 2011

(65) Prior Publication Data

US 2011/0287383 A1 Nov. 24, 2011

Related U.S. Application Data (63) Continuation of application No. 12/426,419, filed on Apr. 20, 2009, now abandoned, which is a continuation of application No. 11/716,441, filed on Mar. 9, 2007, now abandoned.

(51) Int. Cl.
*A61C 13/225* (2006.01)
*A61C 8/00* (2006.01)

(52) U.S. Cl.
USPC ........................................ 433/173; 433/201.1

(58) Field of Classification Search
USPC ....................... 433/172–176, 180–183, 201.1
See application file for complete search history.

(56) References Cited

U.S. PATENT DOCUMENTS

| | | |
|---|---|---|
| 4,252,525 A | 2/1981 | Child |
| 4,668,191 A | 5/1987 | Plischka |
| 4,932,868 A | 6/1990 | Linkow |
| 4,934,935 A | 6/1990 | Edwards |
| 5,049,073 A | 9/1991 | Lauks |
| 5,102,336 A | 4/1992 | Linkow |
| 5,316,477 A | 5/1994 | Calderon |
| 5,344,457 A | 9/1994 | Pilliar et al. |
| 5,458,488 A | 10/1995 | Chalifoux |
| 5,549,475 A | 8/1996 | Duerr |
| 5,571,016 A | 11/1996 | Ingber et al. |
| 5,620,323 A | 4/1997 | Bressman |
| 5,667,384 A * | 9/1997 | Sutter et al. .................. 433/172 |
| 5,882,200 A | 3/1999 | Sutter et al. |
| 5,931,675 A | 8/1999 | Callan |
| 6,024,567 A | 2/2000 | Callan |
| 6,164,969 A * | 12/2000 | Dinkelacker .................. 433/173 |
| 6,527,554 B2 | 3/2003 | Hurson et al. |
| 2003/0232309 A1* | 12/2003 | Dinkelacker .................. 433/173 |
| 2004/0043360 A1* | 3/2004 | Obata ............................ 433/173 |
| 2006/0105296 A1* | 5/2006 | Linder et al. ................. 433/173 |

FOREIGN PATENT DOCUMENTS

FR 2634369 1/1990

* cited by examiner

*Primary Examiner* — Todd Manahan
*Assistant Examiner* — Michael R Ballinger
(74) *Attorney, Agent, or Firm* — Stetina Brunda Garred & Brucker (57) ABSTRACT

A dental prosthesis comprises an implant, an abutment and a crown. The implant has distal and proximal portions with the implant proximal portion including distal and proximal segments. The implant proximal segment has an outer surface. The abutment has distal and proximal segments and defines an abutment shoulder therebetween. The abutment shoulder is configured to circumferentially engage the outer surface of the implant proximal segment such that an implant abutment joint is defined therebetween. The crown is configured to be positioned over the abutment and the implant such that the crown covers the implant abutment joint. The implant proximal segment has an annular concave cross-section such that the crown distal end has a rounded shape to reduce the potential for stress cracking of the crown.

16 Claims, 4 Drawing Sheets

DENTAL IMPLANT

CROSS-REFERENCE TO RELATED APPLICATIONS

The present invention is a continuation of U.S. patent application Ser. No. 12/426,419 entitled DENTAL IMPLANT filed Apr. 20, 2009 and is abandoned which is a continuation of U.S. patent application Ser. No. 11/716,441 entitled DENTAL IMPLANT filed Mar. 9, 2007 and is abandoned, the entirety of the disclosures of which are expressly incorporated herein by reference.

STATEMENT RE: FEDERALLY SPONSORED RESEARCH/DEVELOPMENT (Not Applicable)

BACKGROUND

The present invention relates generally to dental prostheses and, more particularly, to a dental prosthesis including an implant, an abutment which is attachable to the implant, and a crown which is attachable to the abutment and the implant such that the joint defined between the abutment and the implant is covered and effectively sealed.

As is well known in the art, dental prostheses are commonly used in the dental field to address extensive damage to teeth caused by injury or disease. A typical dental prosthesis comprises an implant, an abutment and a crown. The implant itself generally comprises a metallic component which is implanted or embedded into the bony structure of a patient's mouth subsequent to the removal of the damaged tooth alone or in combination with one or more adjacent teeth. The installation of the implant is typically initiated by forming a hole in the bony structure and then embedding the implant into the bony structure by screwing the implant into the hole via threads formed on an exterior of the implant.

After the implant has been embedded into the bony structure, the bone normally recovers and grows around the implant, thus resulting in bone/implant integration. To enhance the integration of the implant into the bone, the implant may be coated with a surface finish such as etched titanium and/or a biocompatible coating such as hydroxylapatite (HA). Subsequent to the embedding of the implant into the bony structure, the abutment is attached to the implant. Such attachment may be accomplished through the use of a cement, by the engagement of complementary male and female threads formed on or in the abutment and implant, or by the mating of corresponding tapers or other geometries formed on or in the abutment and implant.

When attached to the implant, a portion of the abutment extends above the gum line of the patient for purposes of facilitating attachment of the crown to the implant. If the implant is embedded into the bony structure such that the implant is completely disposed below or submerged within the gum line of the patient, the attachment of the abutment to the implant requires a second surgical procedure for purposes of accessing the implant. However, if the implant is embedded into the bony structure in a manner wherein a portion thereof protrudes above the patient's gum line, then the attachment of the abutment may be accomplished without the need for the second surgical procedure, thus requiring only the initial surgical procedure to complete the implantation or embedding process.

As was previously indicated, the crown of the dental prosthesis is attached to that portion of the abutment which extends above the patient's gum line. In the prior art, crowns are fabricated and installed in accordance with well-established procedures which include taking a transfer impression of the exposed portion of the abutment to establish with precision its configuration and orientation, thus insuring a complete attachment of the crown thereto. The exposed portion of the abutment to which the crown is attached may have the natural form of a prepared tooth, or an artificial form of a particular geometry adapted to achieve a secure attachment of the crown. The attachment of the crown to the abutment is typically accomplished through the use of an adhesive and/or cement, or through the engagement of corresponding male and female threads on or in the crown and abutment to each other. The attachment of the crown to the abutment completes the assembly of the dental prosthesis.

As will be recognized from the aforementioned description of the dental prosthesis, the assembly thereof results in the formation of several joints. These joints include the joint formed by the attachment of the crown to the abutment, and the joint formed by the attachment of the abutment to the implant. Of these joints, that joint considered most important in relation to the long-term viability of the prosthesis is the joint between the implant and the abutment which is commonly referred to as the implant abutment joint or "IAJ".

Recent research in the dental field has suggested that the IAJ plays a key role in bone loss around the implant. Though such bone loss has not been well studied or well documented, it is believed to be a common occurrence which is at least partially attributable to the IAJ serving as a site for bacterial invasion and colonization. Over time, such bone loss can compromise the integrity of the implant or cause its failure by breaking loose from the bony structure into which the implant is embedded.

Obviously, such failure, in addition to providing inconvenience and discomfort for the patient, is of serious medical concern due to the resulting bone loss or mutilation potentially rendering the installation of a replacement implant difficult or impossible. The joint formed by the attachment of the crown to the abutment is also susceptible to bacterial invasion which contributes to bone loss around the implant.

The present invention addresses the susceptibility of the IAJ and the crown/abutment joint to bacterial infestation by providing a dental prosthesis which is configured to effectively cover and seal these joints. In addition, the dental prosthesis of the present invention also prevents micro-movement between the abutment and the implant at the IAJ which, under the forces of mastication (i.e., chewing), can result in the development of micro-gaps at the IAJ. Such micro-gaps can harbor bacteria which can lead to inflammation and, ultimately, failure of the implant.

BRIEF SUMMARY

Provided is a dental prosthesis which comprises an implant, an abutment and a crown. The implant is adapted to be embedded into the bony structure of a patient's mouth. The abutment is attached to the implant in a manner wherein an implant abutment joint is defined therebetween. The crown is attached to the abutment and the implant in a manner wherein the implant abutment joint is covered by the crown. The attachment of the crown to the abutment and implant may be facilitated through the use of adhesive (e.g., dental cement) extending between the crown and the implant (i.e., crown implant joint).

The adhesive within the crown implant joint effectively seals the implant abutment joint as well as protects the crown implant joint. More particularly, the adhesive isolates such joints from the gum line in the patient in order to prevent migration of bacteria into the joints. The implant has distal and proximal portions with the implant proximal portion including distal and proximal segments. The implant proximal segment includes an outer surface. The abutment also has distal and proximal portions with distal and proximal ends being disposed respectively adjacent thereto. The abutment distal and proximal portions define an abutment shoulder therebetween.

Importantly, the abutment shoulder is configured to circumferentially engage the outer surface of the implant proximal segment with increased joint surface area which thereby improves joint strength. In addition, the circumferential engagement between the abutment shoulder and the implant provides improved resistance to micro-movement of the abutment relative to the implant. The elimination of such micro-movement reduces the risk of cracking of the adhesive and also minimizes the development of micro-gapping at the joint which, in turn, reduces the potential for periodontal pathogens. The implant abutment joint and the crown implant joint are sealed from bacterial invasion due to the positioning of the crown over the abutment and implant.

The implant may be comprised of an elongate, externally threaded implant distal portion which is insertable into the bony structure of the patient's mouth. The implant proximal portion itself includes distal and proximal segments. The implant distal segment may have a generally cylindrical outer surface or it may be circumferentially undercut. The circumferential undercut which defines the implant distal segment interconnects the implant distal portion to the implant proximal segment. The implant proximal segment may have an outer surface which may be tapered or concave.

If tapered, the implant proximal segment is preferably conically shaped at an angle of about 45° although other angles are contemplated. More preferably, the implant proximal segment is formed at an angle of less than about 45° and greater than about 3° relative to an axis of the implant. If concave, the implant proximal segment may itself include conical portions which interface with the crown and are therefore preferably formed at the above-mentioned half-angles of between about 45° and 3° to avoid cracking of adhesive between the crown and implant while eliminating the need for overly-tight manufacturing tolerances which increase manufacturing costs.

The abutment may include an abutment cavity formed in the abutment proximal portion adjacent to the abutment shoulder. Preferably, the abutment cavity is formed complementary to the outer surface of the implant proximal segment in order to facilitate the circumferential engagement of the abutment shoulder to the outer surface. The abutment proximal portion engages the outer surface of the implant proximal segment at a lower end of the abutment proximal portion. Additionally, it is contemplated that the abutment cavity may be configured to engage the outer surface of the implant proximal segment in surface-to-surface or edge-to-surface contact therebetween.

The abutment distal portion defines an abutment shaft. Extending axially within the implant proximal end is an implant bore which is sized and configured to receive the abutment shaft. In one embodiment, the implant bore may have a generally circular cross-sectional configuration with the abutment shaft being of complementary cylindrical configuration although other configurations are contemplated. The abutment distal portion or abutment shaft may be advanced into the implant bore and may be secured therewithin through the use of adhesive.

Alternatively, the implant bore may be internally threaded with the abutment distal portion or abutment shaft being externally threaded to facilitate threadable engagement therebetween. The abutment proximal portion may have a frustoconically shaped outer surface such that the abutment forms a truncated cone. The abutment may optionally include an abutment neck formed adjacent the abutment shoulder and which has a generally reduced cross-sectional area in an axial orientation as compared to the cross-sectional configuration of the immediately adjacent portions of the abutment. Advantageously, the abutment neck minimizes the overall size of the abutment while still providing a configuration which may effectively engage the outer surface of the implant proximal segment.

The crown of the dental prosthesis includes a crown distal portion which itself defines a crown distal end having a crown cavity disposed therewithin. The crown cavity has a shape which is complementary to the outer surface of the abutment proximal portion as well as the outer surface of the implant proximal segment. Receipt of the abutment proximal portion and implant proximal segment into the crown cavity results in engagement of the crown distal portion to the implant proximal segment via direct contact therebetween. In this manner, the implant abutment joint defined between the abutment proximal portion and the implant proximal end is covered and may be thereafter sealed through the use of adhesive.

In a further embodiment, the implant proximal segment may have a generally circumferential or annular concave cross-section such that the crown distal end can be provided with a complementary rounded or blunt circumferential edge instead of a less desirable circumferential knife edge configuration. The rounded shape of the crown distal end provides increased surface to more uniformly distribute occlusal forces applied to the joint.

As was mentioned above, such occlusal forces are typically the result of mastication (i.e., chewing) and are transmitted in an axial direction from the crown to the implant. The uniform distribution of the occlusal forces at the crown distal end reduces the susceptibility of a failure of the crown distal end due to overstressing and cracking. In addition, formation of the concave cross-section on the implant proximal segment may further reduce the loads placed on the adhesive which may lead to the failure of the adhesive joint between the crown distal end and the implant proximal segment.

Further, in accordance with the dental prosthesis, there is provided a method of installing the dental prosthesis into a patient comprising the initial step of drilling a hole into the bony structure of the patient's mouth or oral cavity. Thereafter, the implant of the dental prosthesis may be threaded into the hole in the bony structure. The abutment may then be attached to the implant in a manner wherein the implant abutment joint is defined between the abutment and the implant.

The layer of adhesive may be applied to exposed portions of the abutment and the implant which interface with the crown cavity. The crown may then be attached to the abutment and the implant in a manner wherein the implant abutment joint is covered by the crown. The flow of adhesive between the crown and the implant seals the implant abutment joint as well as the joint between the crown and the implant. The abutment may be joined to the implant through the use of the adhesive and/or via threadable engagement.

BRIEF DESCRIPTION OF THE DRAWINGS

These and other features and advantages of the various embodiments disclosed herein will be better understood with respect to the following description and drawings in which like numbers refer to like parts throughout and in which.

DETAILED DESCRIPTION

Referring now to the drawings wherein the showings are for purposes of illustrating various embodiments of the present invention only and not for purposes of limiting the same, FIGS. 1-11 depict a dental prosthesis 10 which, in its broadest sense, comprises an implant 20, an abutment 50 and a crown 80. The implant 20 is adapted to be embedded into the bony structure of a patient's mouth or oral cavity. The implant 20 itself includes an elongate implant distal portion 26 which defines an implant distal end 22. The implant distal portion 26 may be further divided into an implant body 32 and an implant trunk 31. The implant distal portion 26 may further include external threads 33 formed on the implant body 32 which are preferably configured to be threadably engaged to the bony structure.

The implant 20 may further include an implant neck or implant proximal portion 28. As can be seen in the figures, the implant proximal portion 28 is separated from the implant trunk 31 by an annular implant shoulder 30. Depending on the specific configuration of the implant proximal portion 28, the cross-sectional area of the implant proximal portion 28 may slightly exceed the cross-sectional area of the implant trunk 31 resulting in the formation of the annular implant shoulder 30 therebetween. As was earlier mentioned, the implant trunk 31 is disposed above the implant body 32 and serves as the portion of the implant 20 that connects the implant body 32 to the implant proximal portion 28.

The implant proximal portion 28 itself may be comprised of an implant distal segment 37 and an implant proximal segment 34. The implant distal and proximal segments 37, 34 converge at a prosthetic margin 40. The implant proximal portion 28 further defines an implant proximal end 24 which may include an implant bore 42 formed therewithin. The implant bore 42 may have a variety of axial cross-sectional configurations such as hexagonal and/or cylindrical cross-sections and is generally configured to extend axially at least partially through the implant proximal portion 28 and into the implant distal portion 26. As can be seen in the figures, the implant bore 42 may extend to approximately the mid-point of the implant distal portion 26.

The implant 20 may be fabricated from a metallic material which is preferably a biocompatible material such as titanium or other suitable materials. Additionally, certain areas of the implant 20 such as the implant distal portion 26 may be coated with hydroxylapitite (HA) or other suitable biocompatible materials in order to assist in the integration of the implant 20 to the bony structure of the patient's mouth. Additionally, the implant distal portion 26 may be etched with a suitable acid or other solution. The implant 20 may be provided in a wide variety of sizes to accommodate dental structures of the patient. In this regard, the implant 20 may be provided in a diameter of between about 3.5 millimeter (mm) to about 6.0 mm although other sizes are contemplated to fit different patients. Likewise, the implant 20 may be provided in a variety of lengths such as from about 10 mm to about 16 mm although longer and shorter lengths are contemplated.

The dental prosthesis 10 further includes the abutment 50 which may be attached to the implant 20 in a manner to be described in greater detail below. The abutment 50 itself may comprise an elongate, cylindrically configured, shaft-like abutment distal portion 56 and an abutment proximal portion 58. The abutment proximal portion 58 may have a frusto-conical outer surface. As such, the abutment proximal portion 58 may take the form of a truncated cone although other shapes are contemplated. In the dental prosthesis 10, the abutment distal portion 56 is preferably sized and configured as an abutment shaft 66 such that an outer surface thereof is configured complementary to the implant bore 42. More specifically, the abutment shaft 66 may be provided with a cylindrical shape having an outer diameter that is slightly less than that of the implant bore 42.

Adhesive 100 may be applied to the abutment distal portion 56 prior to its advancement into the implant bore 42. Alternatively or in combination therewith, adhesive 100 may be injected into the implant bore 42 prior to the insertion of the abutment distal portion 56 thereinto. The implant bore 42 may be sized and configured to provide a gap between an abutment distal end 52 and a bottom of the implant bore 42 such that adhesive 100 may accumulate and harden, thereby strengthening the bond between the abutment 50 and the implant 20. As can be seen, the advancement of the abutment distal portion 56 into the implant bore 42 is terminated by the engagement of the abutment proximal portion 58 to the implant proximal end 24 (i.e., by direct contact therebetween) and forming the implant abutment joint 44.

As will be described in greater detail below, the unique geometries of the implant proximal portion 28 in combination with the geometry of the abutment distal end 52 results in an improved interface at the implant abutment joint 44. As was earlier mentioned, the implant abutment joint 44 is specifically configured to prevent or reduce micro-movement between the abutment 50 and implant 20 which, in turn, prevents micro-movement between the crown 80 and the implant 20. Such micro-movement is typically the result of forces of mastication in an occlusal or axial direction (i.e. parallel to the implant longitudinal axis). Over time, such micro-movement may result in micro-gapping between the crown 80 and tooth which may cause the adhesive 100 to crack under the load and which may then allow the harboring of bacteria in the joints of the dental prosthesis 10 and the premature failure thereof in addition to formation of periodontal pathogens.

Advantageously, the dental prosthesis 10, in at least one embodiment, is uniquely configured to provide circumferential engagement of the abutment distal end 52 to the implant proximal segment 34 to prevent micro-movement therebetween. As was earlier mentioned, such circumferential engagement of the abutment distal end 52 to the implant proximal segment 34 provides for a more uniform and even distribution of occlusal forces that are exerted by the crown 80 upon the implant 20. Such forces on the crown 80 are transmitted to the abutment 50 and to the implant 20 at respective ones of the implant abutment joint 44 and the crown implant joint.

More particularly, the circumferential engagement of the abutment 50 to the implant 20 provides greater surface area of engagement between the implant 20 and the abutment 50 which increases its resistance to micro-movement therebetween. In addition, the configuration of the crown implant joint allows for a reduction in the force per unit area. The reduced force per unit area reduces susceptibility of adhesive 100 failure (i.e., cracking of the adhesive 100) between the crown 80 and the implant 20 such as may occur due to overloading of the adhesive 100 bond over time. Furthermore, the circumferential engagement of the abutment distal end 52 to the implant proximal segment 34 reduces stress cracking of the crown 80 at its crown distal end 82 in direct contact with the implant 20.

As can be seen in the figures, due to the configuration of an outer surface of the implant proximal segment 34 and the complementary mating surfaces of the abutment proximal portion 58, when the abutment 50 is attached to the implant 20 in the above-described manner, the abutment 50 is generally in continuous circumferential engagement such that outer surfaces thereof are in flush relationship to one another.

The dental prosthesis 10 further comprises the crown 80 which is preferably fabricated from an inert biocompatible material such as ceramic and/or metal and is preferably configured in a desired exterior surface configuration in a manner known in the art. The crown 80 includes a crown distal portion 86 which defines the crown distal end 82. Disposed within the crown distal end 82 is a crown cavity 90 which is configured complementary to the abutment proximal portion 58 and the implant proximal segment 34.

Depending on the configuration of the implant 20 and the abutment 50, the crown cavity 90 may include an annular crown chamfer 92 which is specifically configured to circumferentially engage the implant proximal segment 34 and/or an abutment shoulder 60 disposed between the abutment distal and proximal portions 56, 58. As will be described in greater detail below, the crown cavity 90 is adapted to engage the abutment proximal portion 58 and therefore has a shape which is complementary thereto. Additionally, the crown chamfer 92 is adapted to receive the implant proximal segment 34 and therefore has a shape which is complementary thereto.

In the dental prosthesis 10, attachment of the crown 80 to the abutment 50 and/or implant 20 is facilitated through the use of an adhesive 100 which may be applied to the outer surface of the abutment proximal portion 58 and may include the application of adhesive 100 to the abutment proximal end 54. Furthermore, adhesive 100 may be applied to the implant proximal segment 34. The crown 80 is then advanced over the abutment 50 and implant 20 such that the abutment proximal portion 58 is snugly received into the crown cavity 90 and the crown distal end 82 is circumferentially engaged to the abutment proximal segment. Ideally, the crown 80 is sized and configured such that when the abutment proximal portion 58 is fully received into the crown cavity 90 and the crown distal end 82 is engaged to the implant proximal segment 34, the crown distal end 82 extends to and terminates at the prosthetic margin 40 defined between the implant distal segment 37 and implant proximal segment 34.

When the crown 80 is attached to the abutment 50 and implant 20 in the above-described manner, the crown distal end 82, by virtue of its extension to the prosthetic margin 40, is distal to (i.e., extended below) the implant abutment joint 44 resulting in the crown distal portion 86 completely covering the implant abutment joint 44. Additionally, the adhesive 100 for securing the crown 80 to the abutment proximal portion 58 and implant proximal segment 34 preferably extends between the outer surface of the implant proximal segment 34 and the crown cavity 90 adjacent the crown distal end 82. Importantly, upon curing and/or hardening of the adhesive 100, the implant abutment joint 44 is effectively sealed and thereby isolated from the deleterious effects of bacterial invasion, plaque and disease.

The cured and/or hardened adhesive 100 also prevents bacterial migration between the crown 80 and implant 20 by sealing the joint between the crown distal portion 86 and implant proximal segment 34. Also, sealed by the curative adhesive 100 is the joint between the crown 80 and the abutment proximal portion 58. Thus, the adhesive 100 serves several essential purposes which includes attachment of the crown 80 to the abutment 50 and implant 20, sealing of the implant abutment joint 44, and sealing of the crown implant joint for purposes of preventing bacterial invasion.

Figure 1:
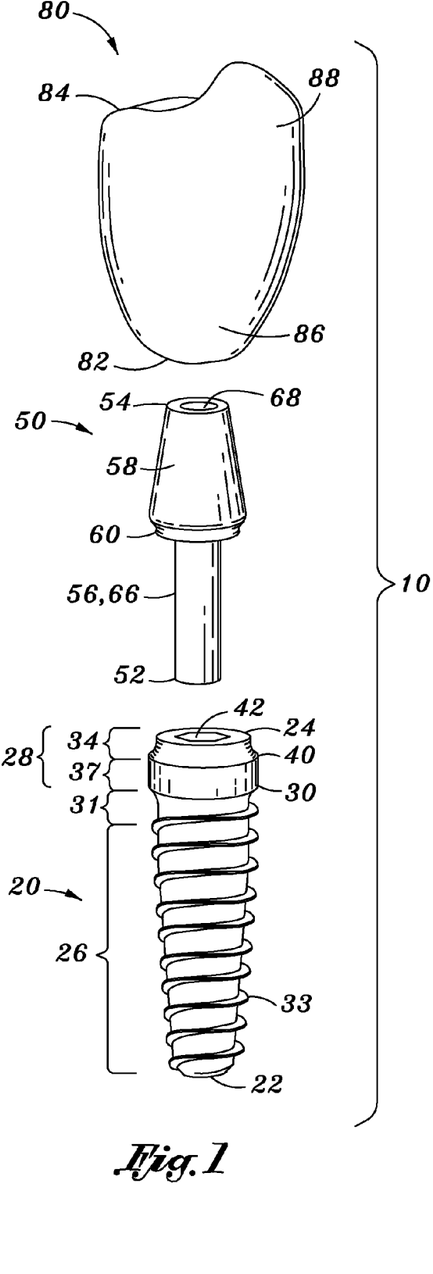
FIG. 1 is an exploded perspective view of a dental prosthesis constructed in accordance with an embodiment and illustrating an implant, an abutment and a crown of the dental prosthesis.
Figure 2:
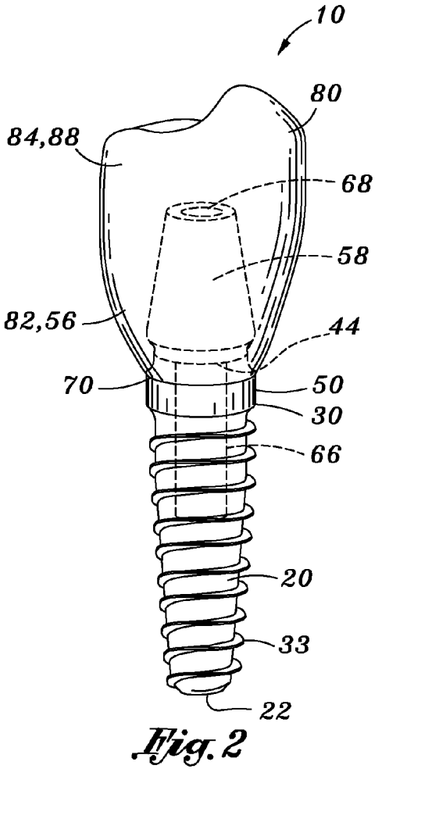
FIG. 2 is a perspective view of the dental prosthesis of FIG. 1 in an assembled state.
Figure 3:
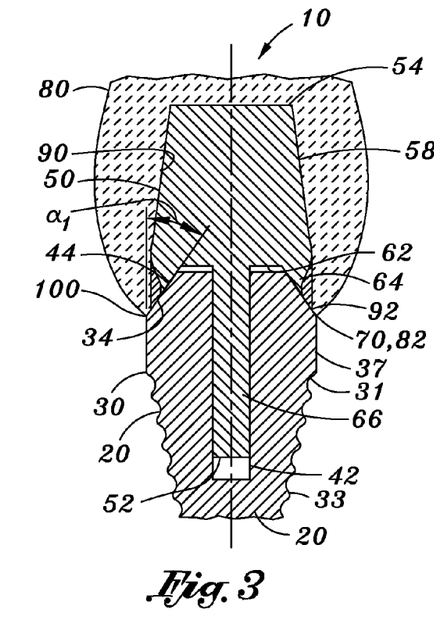
FIG. 3 is a cross-sectional partial view of the dental prosthesis and illustrating an implant proximal segment and circumferentially engaging with an abutment shoulder and further illustrating the crown being positioned over the abutment and implant and covering an implant abutment joint.

Referring more particularly now to FIG. 3, shown is the dental prosthesis 10 wherein the abutment distal end 52 is specifically configured to circumferentially engage the implant proximal segment 34. More particularly, FIG. 3 illustrates an embodiment of the dental prosthesis 10 wherein the implant proximal segment 34 includes an outer surface which is tapered. More specifically, the tapered outer surface of the implant proximal segment 34 may be conically shaped in order to facilitate circumferential engagement of the abutment distal end 52 thereto. In one embodiment, the implant proximal segment 34 may be provided at an angle indicated by the reference character $\alpha_1$ as shown in FIGS. 3 and 10a. Although the implant proximal segment 34 may be provided in any configuration, the angular range for $\alpha_1$ is preferably no greater than about 45° and preferably less than about 3° relative to the implant longitudinal axis.

As can be seen in the figures, the implant distal segment 37 of the dental prosthesis 10 may be generally cylindrically shaped although other configurations for the implant distal segment 37 are contemplated. The implant distal segment 37 is configured to interface with soft tissue surrounding the bony structure into which the implant 20 is embedded. The implant distal segment 37 may have a height of about 1 mm although the implant distal segment 37 may be provided in any height.

Figure 4:
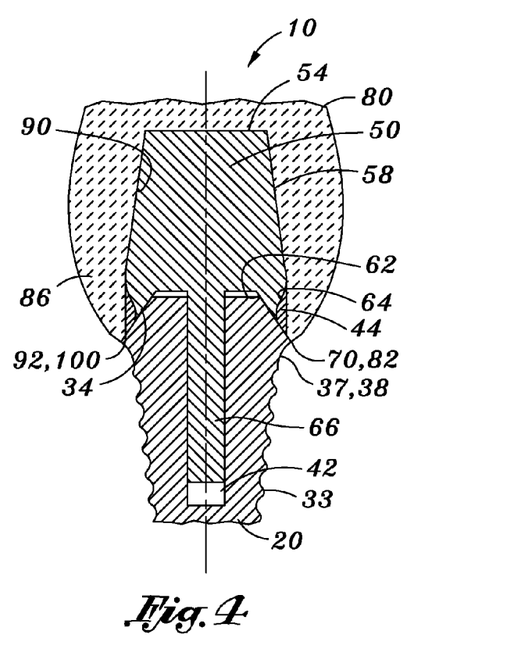
FIG. 4 is a cross-sectional view of the dental prosthesis which is substantially similar to that shown in FIG. 3 but illustrating an implant distal segment having an undercut configuration generally configured as a continuous radius.
Figure 5:
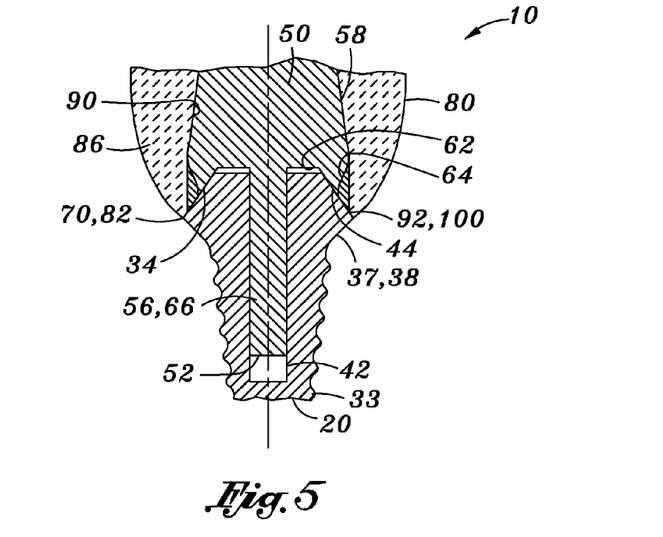
FIG. 5 is a cross-sectional view of the dental prosthesis in a configuration similar to FIG. 4 but illustrating the undercut configured as a short conical portion transitioning into an implant body via a circumferential radius.
Figure 6:
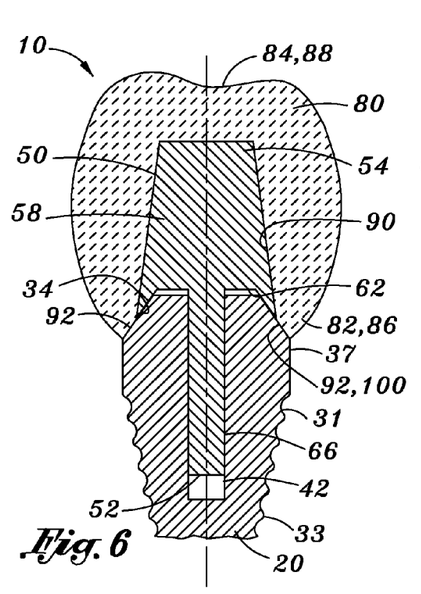
FIG. 6 is a cross-sectional view of the dental prosthesis substantially similar to that which is shown in FIGS. 3 and 4 but omitting an abutment neck of the abutment.
Figure 7:
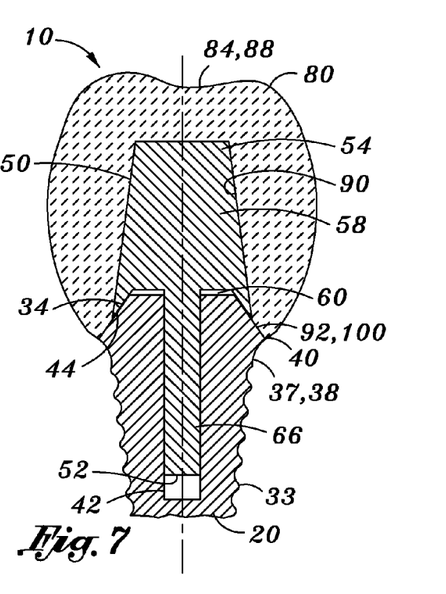
FIG. 7 is a cross-sectional view of the dental prosthesis substantially similar to that shown in FIG. 6 but including the configuration of the implant having the undercut as shown in FIG. 4.

Alternatively, as shown in FIGS. 4-5, the implant distal segment 37 may define a circumferential or annular undercut 38 between the implant distal portion 26 and the implant proximal segment 34. In this configuration of the dental prosthesis 10, the implant distal segment 37 is interposed between the implant trunk 31 and the implant proximal segment 34 and interconnects the two. The circumferential undercut 38 as shown in FIGS. 4-5 may have an arcuately shaped cross-section.

Such arcuate cross-section may be defined by a continuous radius extending from the prosthetic margin 40 (i.e., at the convergence of the implant distal and proximal segments 37, 34) and blending into the implant trunk 31. Alternatively, the circumferential undercut 38 of the implant distal segment 37 may be defined by a short conical or tapered surface which extends from the prosthetic margin 40 toward the implant trunk 31 and which blends into the implant trunk 31 by an annular radius.

As shown in FIGS. 1-9a, the abutment shoulder 60 is specifically configured to circumferentially engage the outer surface of the implant proximal segment 34. The abutment 50 may include an abutment cavity 62 for at least partially receiving the outer surface of the implant proximal segment 34. As shown in FIGS. 3-7, the outer surface of the implant proximal segment 34 may be tapered and the abutment cavity 62 may have a conical shape in order to interface with the outer surface of the implant proximal segment 34. Optionally, the abutment cavity 62 may have a conical shape with a half angle that is slightly smaller than the half angle of the outer surface of the implant proximal segment 34.

In this manner, only a lower edge of the abutment proximal portion 58 may engage the implant proximal segment 34 outer surface in edge-to-surface contact. Optionally, the abutment 50 and outer surface of the implant proximal segment 34 may be configured with substantially equal half angles to provide surface-to-surface contact between the abutment 50 and the implant 20. However, it is contemplated that the abutment cavity 62 may be provided in a variety of alternative shapes and sizes to provide the feature of circumferential engagement therebetween. As was earlier mentioned, such configuration is believed to uniformly distribute occlusal forces imposed on the crown 80 and also provide a greater area through which forces may be transferred between the abutment 50 and the implant 20.

The abutment 50 may further include an abutment neck 64 disposed adjacent the abutment distal end 52 and the abutment shoulder 60. The abutment neck 64 preferably has a reduced cross-section in an axial direction relative to the cross-section of an immediately adjacent portion of the abutment 50. More particularly, the abutment neck 64 provides a locally thinned area of the abutment 50 which allows for a reduction in the overall volume occupied by the abutment 50 within the crown cavity 90 but while still providing for circumferential engagement of the abutment shoulder 60 to the outer surface of the implant proximal segment 34. In the figures, the abutment 50 can be seen as having a generally frusto-conical configuration while allowing the abutment proximal portion 58 outer surface to blend in with the implant proximal segment 34.

The crown 80 includes a crown distal portion 86 which defines the crown distal end 82 having the crown cavity 90 formed therein. The crown cavity 90 is configured to be complementary to the abutment proximal segment such that the crown distal end 82 may also circumferentially engage the implant proximal segment 34 as shown in FIGS. 1-9a. As was earlier mentioned, receipt of the abutment proximal portion 58 and abutment proximal segment into the crown cavity 90 results in engagement of the crown distal portion 86 to the implant proximal segment 34 outer surface such that the crown implant joint is defined therebetween. The implant abutment joint 44 is covered by the crown distal portion 86 and a layer of adhesive 100 may be disposed between the implant proximal segment 34 and the crown cavity 90 at the crown implant joint in order to provide sealing engagement therebetween.

Regarding joining of the abutment 50 to the implant 20, the abutment distal portion 56 may be externally threaded with the abutment proximal portion 58 including a recess disposed within the abutment proximal end 54 for receiving an implement such as a screwdriver to threadably rotate the abutment 50. Additionally, the implant bore 42 may be internally threaded. As such, attachment of the abutment 50 to the implant 20 may be facilitated by threadable receipt of the abutment distal portion 56 into the implant bore 42. Optionally, adhesive 100 may be provided between the implant bore 42 and the abutment distal portion 56 or abutment shaft 66 in order to secure the two components.

Figures 8, 8A:
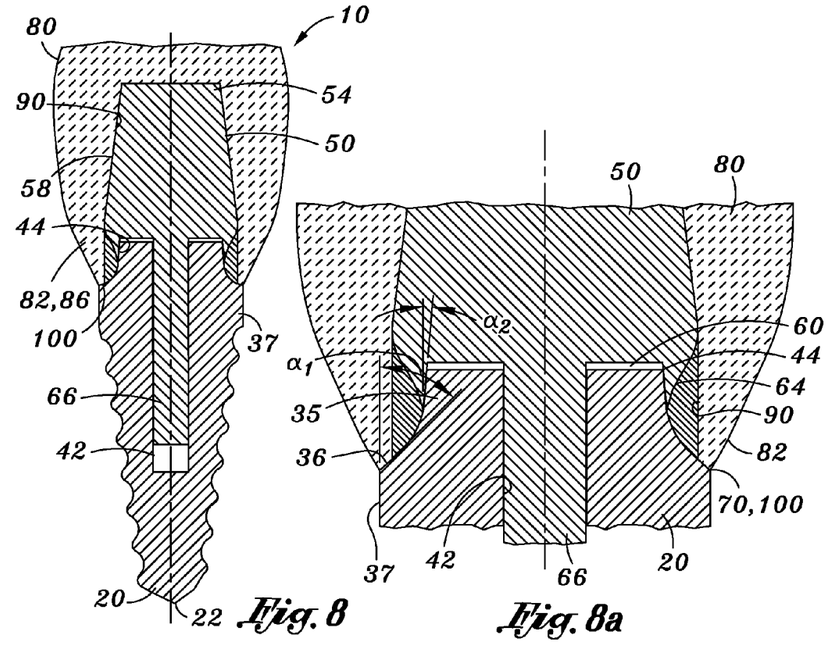
FIG. 8 is a cross-sectional view of the dental prosthesis and illustrating the implant proximal segment having a concave cross-section.
FIG. 8a is an enlarged cross-sectional view of the dental prosthesis illustrating the implant abutment joint.
Figure 9:
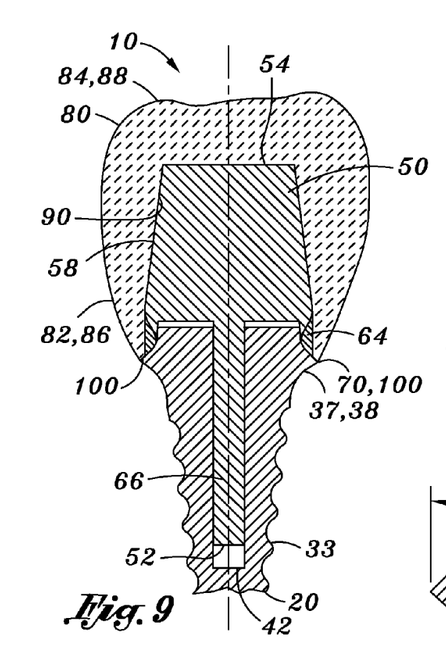
FIG. 9 is a cross-sectional view of the dental prosthesis substantially similar to that which is shown in FIG. 8 but including the configuration of the implant having the undercut as shown in FIG. 4.
Figure 9A:
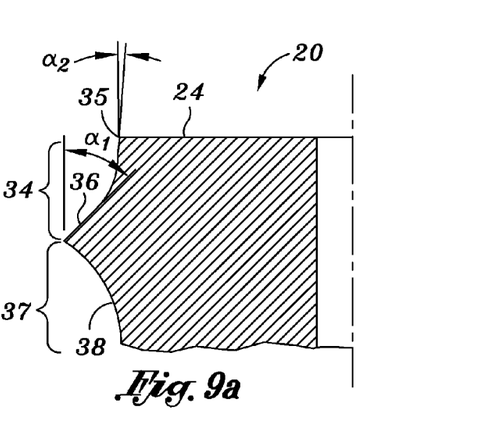
FIG. 9a is an enlarged cross-sectional view of the abutment of FIG. 9.

As can be seen in FIGS. 1-2 and 8-9a, in a further embodiment, the implant proximal segment 34 may have an annular concave cross-sectional shape. The implant proximal segment 34 is configured to provide an arcuate interface between the implant proximal segment 34 and the implant distal segment 37 (i.e., at the prosthetic margin 40). As shown in FIG. 9a, the concave cross-section of the implant proximal segment 34 may be defined by a radius extending directly upwardly from a tangent of the radius. Preferably, the radius intersects the prosthetic margin 40 at an angle indicated by reference character $\alpha_1$ and which is preferably no greater than about 45° relative to the implant longitudinal axis and no less than about 3° relative to the implant longitudinal axis.

By limiting the angular orientation of the implant proximal segment 34 to no greater than about 45°, the magnitude of vertical forces transmitted from the crown 80 into the implant 20 across the adhesive 100 may be minimized. By minimizing the magnitude of these vertical forces on the adhesive 100, the risk of cracking the adhesive is avoided. In addition, limiting the angular orientation of the implant proximal segment 34 to no greater than about 45° reduces the risk of stress-cracking and resultant fracturing of the crown 80 at the crown distal end 82 where the crown 80 engages the implant proximal segment 34. On the other hand, by limiting the angular orientation of the implant proximal segment 34 to no less that about 3° reduces or eliminates the need for overly-tight manufacturing tolerances of the crown 80 and/or implant 20.

More specifically, maintaining the angular orientation of the implant proximal segment 34 to no less that about 3° allows for installation of the dental prosthesis 10 in keeping with material and methods of dentistry known in the art. Finally, limiting the angular orientation to no less than about 3° reduces the risk of adhesive 100 cracking and failure thereof between the crown 80 and implant 20 and/or abutment 50 which would otherwise compromise the structural integrity of the crown implant joint and/or crown abutment joint. It should be noted that the range of angular orientation described above for the implant proximal segment 34 are applicable to all configurations of the dental prosthesis 10 shown and described herein.

As can be seen in FIG. 9a, the radius may transition into an upper conical surface 35 of the implant proximal segment 34. Preferably, the upper conical surface 35 is formed at an angle indicated in FIG. 9a by the reference character $\alpha_2$ of at least about 3°, as discussed above, although it is contemplated that the upper conical surface 35 may be formed at the angular orientation of no greater than about 45° relative to the implant longitudinal axis. The concave cross-section of the implant proximal segment 34 provides a relatively large area upon which forces from the crown 80 may be distributed into the implant 20. The concave cross-section provides a relatively large surface area and, therefore, results in reduced force per unit area that must be carried by the adhesive 100 which bonds the crown 80 to the implant 20. In this manner, the concave cross-section of the implant proximal segment 34 eliminates or prevents failure or fracturing of the adhesive 100.

The implant proximal segment 34 may be defined by the previously-mentioned upper conical surface 35 and a lower conical surface 36 disposed adjacent the prosthetic margin 40. The lower conical surface 36 may preferably extend upwardly from the prosthetic margin 40 at an angle $\alpha_1$ of no greater than about 45° although other angles are contemplated. As was earlier mentioned, the upper conical surface 35 extends downwardly from the implant proximal end 24 and intersects the annular radius which also transitions into the lower conical surface 36.

As can be seen in FIG. 9a, the upper and lower conical surfaces 35, 36 may be joined via a circumferential radius. Preferably, the concave cross-section is configured such that the tangent is offset radially inwardly from the prosthetic margin 40 by about 0.2 mm to about 1.0 mm. Such offset is believed to provide an optimal joint configuration and may reduce or eliminate adhesive 100 failure such as by cracking between the crown 80 and the implant proximal segment 34. The crown distal end 82 may have a radiused configuration formed complementary to the implant proximal segment 34 in order to eliminate stress over time.

As was earlier mentioned, the dental prosthesis 10 as shown in FIGS. 1-9a, may be configured such that the abutment shoulder 60 is configured to circumferentially engage the outer surface of the implant proximal segment 34. In this regard, the abutment 50 includes the abutment cavity 62 which is likewise formed to be complementary to the outer surface of the implant proximal segment 34 to enable circumferential engagement therebetween. As was earlier mentioned, such engagement may be a surface-to-surface or surface-to-line circumferential engagement. If an abutment neck 64 is provided in the abutment 50, the abutment neck 64 is preferably configured to blend into the upper and lower conical surfaces 35, 36 and radius of the implant proximal segment 34. The abutment recess 68 may be further provided in the abutment 50 in order to facilitate insertion of the abutment shaft 66 into the implant bore 42.

Figure 10:
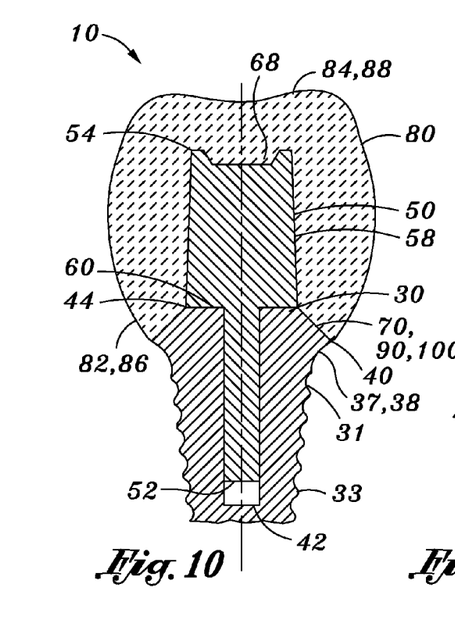
FIG. 10 is a cross-sectional view of the dental prosthesis and which is configured substantially similar to that shown in FIG. 4 but wherein the abutment shoulder is configured to directly engage a top portion of the implant.
Figure 10A:
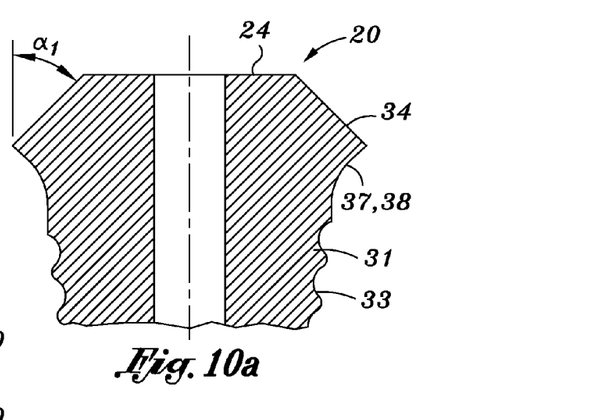
FIG. 10a is an enlarged cross-sectional view of the dental prosthesis of FIG. 10 and illustrating the configuration of the abutment.
Figure 11:
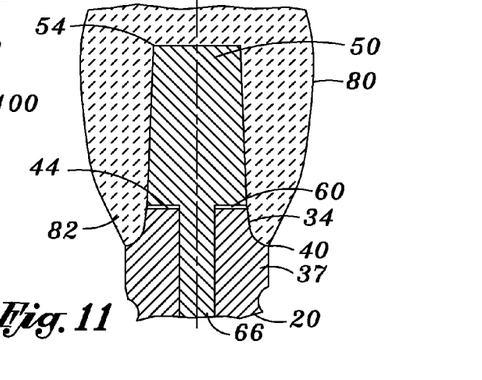
FIG. 11 is a cross-sectional view substantially similar to that shown in FIG. 10 but which includes the configuration of the implant as shown in FIG. 8.

Referring to FIGS. 10-11, the implant proximal segment 34 may be configured such that the abutment shoulder 60 engages an end face of the implant proximal end 24 as opposed to circumferential engagement illustrated in FIGS. 1-9a. As can be seen in FIG. 10, the implant distal segment 37 may include the annular undercut 38 configuration shown in FIGS. 4 and 5 and as described above. The implant proximal segment 34 may have the conical shape described above. As was also described above, the crown 80 covers the implant abutment joint 44 when the crown 80 is mounted on the abutment 50. More specifically, for the configurations shown in FIGS. 10 and 11, the crown 80 is configured to extend over and cover the implant abutment joint 44.

As shown in FIG. 11, the implant distal segment 37 may be configured substantially similar to that shown in FIG. 10 but includes the configuration of the implant proximal segment 34 shown in FIG. 8a. For the configuration shown in FIG. 11 where the implant proximal segment 34 has a concave cross-section, the abutment 50 is preferably configured such that the implant proximal segment 34 is substantially continuous with the outer surface of the abutment proximal portion 58 when the abutment 50 is attached to the implant 20.

Having thus described various embodiments of the dental prosthesis 10 constructed in accordance with the present invention, a method of installing such prosthesis into a patient's mouth will now be described. Installation of the dental prosthesis 10 is initiated by first drilling a hole into the bony structure of the patient's mouth. Thereafter, the externally-threaded implant distal portion 26 may be embedded into the bony structure of the patient's mouth by threadable engagement. The implant 20 is preferably embedded to a level such that the implant proximal segment 34 protrudes above the bony structure. However, the implant proximal segment 34 may be disposed below, at, or above the patient's gum line.

Subsequent to embedding the implant 20 into the bony structure, the abutment 50 is rigidly attached to the implant 20 in the above-described manner and may be accomplished through the use of an adhesive 100 and/or via threadable engagement of the abutment 50 and implant 20 to one another. After attachment of the abutment 50 to the implant 20, a transfer cast is made of exposed portions of the abutment 50 and implant 20. Such exposed portions include the outer surface of the implant proximal segment 34 and the frusto-conical outer surface of the abutment proximal portion 58. The transfer cast is used to fabricate the crown 80 in order to ensure complete coverage of exposed portions of the abutment 50 and implant 20.

Subsequent to fabrication of the crown 80, a layer of the adhesive 100 may be applied to exposed portions of the abutment 50 and implant 20 (i.e., outer surface of the abutment proximal portion 58 and outer surface of the implant proximal segment 34). The crown 80 may be then be attached to those portions of the abutment 50 and implant 20 which are covered by adhesive 100. Such attachment results in the implant abutment joint 44 being completely covered by the crown distal portion 86. Furthermore, such attachment results in the flow of adhesive 100 between the crown cavity 90 and the outer surface of the implant proximal segment 34.

The adhesive 100 preferably extends between the crown cavity 90 and the outer surface of the abutment proximal portion 58. For configurations of the implant 20 wherein the implant proximal segment is formed at an angle $\alpha_2$ as steep as 3° as shown in FIGS. 8a and 9a, the abutment neck 64 results in the creation of an annular void between the crown cavity 90 and the implant 20/abutment 50. Advantageously, such annular void provides an area within which excess adhesive 100 may collect to avoid the undesirable effects of hydraulic pressure build-up of adhesive 100 that may otherwise occur between the crown 80 and implant 20/abutment 50.

The curing of the adhesive 100 results in sealing of the implant abutment joint 44, the crown implant joint, and the abutment crown joint 70. Such sealing eliminates the susceptibility of such joints to bacterial invasion or other deteriorations. Furthermore, the unique interface between the implant proximal segment 34 and the abutment 50 prevents micromovement of the abutment 50 and the crown 80 relative to the implant 20. Furthermore, the integrity of the adhesive 100 is also improved such that the susceptibility to fractures and resultant bacterial invasion is lessened.

The above description is given by way of example, and not limitation. Given the above disclosure, one skilled in the art could devise variations that are within the scope and spirit of the invention disclosed herein. Furthermore, the various features of the embodiments disclosed herein can be used alone or in varying combinations with each other and are not intended to be limited to the specific combination described herein. Thus, the scope of the claims is not to be limited by the illustrated embodiments.

What is claimed is:

1. A dental prosthesis, comprising:
an implant having distal and proximal portions, the implant proximal portion including distal and proximal segments, the implant proximal segment having a tapered outer surface;
an abutment having
a distal portion,
a proximal portion having a first end and an opposing second end disposed adjacent the distal portion of the abutment, the proximal portion having an external concave surface extending from the second end and configured such that the concave surface increases in diameter in an axial direction from the second end toward the first end, the second end being configured to circumferentially engage the outer surface of the implant proximal segment such that an abutment joint is defined therebetween, and
an abutment cavity formed complementary to the outer surface of the implant proximal segment to facilitate circumferential engagement of the abutment to the outer surface of the implant proximal segment; and
a crown configured to be positioned over the abutment and the implant such that the crown covers the implant abutment joint, wherein:
the crown includes a crown distal portion defining a crown distal end having a crown cavity formed therein, and
the crown cavity being configured complementary to at least a portion of the abutment proximal portion such that the crown distal end circumferentially engages the implant proximal segment.

2. The dental prosthesis of claim 1 wherein the tapered outer surface of the implant proximal segment is conically shaped and having a half angle of about 45 degrees.

3. The dental prosthesis of claim 1 wherein the implant distal segment is cylindrically shaped.

4. The dental prosthesis of claim 1 wherein the implant distal segment defines a circumferential undercut between the implant distal portion and the implant proximal segment.

5. The dental prosthesis of claim 4 wherein the undercut has an arcuately shaped cross section.

6. The dental prosthesis of claim 1 wherein:
the receipt of the abutment proximal portion into the crown cavity resulting in the engagement of the crown to the outer surface of the implant proximal segment such that a crown implant joint is defined therebetween;
the implant abutment joint being covered by the crown distal portion;
a layer of adhesive being disposed between the implant proximal segment and the crown cavity at the crown implant joint.

7. The dental prosthesis of claim 1 wherein:
implant proximal portion defines an implant proximal end having an implant aperture disposed therein;
the abutment distal portion being configured to be insertable into the implant aperture.

8. The dental prosthesis of claim 1 wherein the abutment proximal portion has a frusto-conical outer surface.

9. The dental prosthesis of claim 1 wherein the implant proximal segment has a concave cross section.

10. The dental prosthesis of claim 9 wherein:
the implant proximal segment is defined by upper and lower conical surfaces;
the lower conical surface extending upwardly from a prosthetic margin and having a half angle of up to about 45 degrees;
the upper conical surface extending downwardly from the implant proximal end and having a half angle of up to about 5 degrees;
a radius being formed between the upper and lower conical surfaces.

11. The dental prosthesis of claim 10 wherein:
the implant proximal segment has a height of about 1 millimeter (mm);
the upper conical surface intersecting the radius at a tangent thereof;
the concave cross section being configured such that the tangent is offset radially inwardly from the prosthetic margin by about 0.2 mm to about 1 mm.

12. A dental prosthesis, comprising:
an implant having distal and proximal portions, the implant proximal portion including distal and proximal segments, the implant distal segment defining a circumferential undercut between the implant distal portion and the implant proximal segment, the implant proximal segment having a tapered outer surface and an implant proximal end;
an abutment having abutment distal and proximal portions, an abutment cavity and a terminal edge which circumscribes the abutment distal portion, the abutment proximal portion having a concave external surface extending from the terminal edge and decreasing in diameter in a direction from the proximal portion toward the distal portion, the abutment being configured to directly engage the implant proximal end such that an implant abutment joint is defined therebetween and the abutment cavity formed complementary to the tapered outer surface of the implant proximal segment to facilitate circumferential engagement of the abutment to the outer surface of the implant proximal segment; and
a crown configured to be positioned over the abutment and the implant such that the crown covers the implant abutment joint, the crown having a crown distal portion defining a crown distal end having a crown cavity formed therein, and the crown cavity being configured complementary to at least a portion of the abutment proximal portion such that the crown distal end circumferentially engages the implant proximal segment.

13. The dental prosthesis of claim 12 wherein the undercut has an arcuately shaped cross section.

14. A dental prosthesis, comprising:
an implant having distal and proximal portions, the implant proximal portion including distal and proximal segments, the proximal segment having an external concave surface, the implant proximal segment having an implant proximal end;
an abutment having abutment distal and proximal portions and an abutment neck disposed between the distal and proximal portions and at least partially overlapping a portion of the implant when the abutment is engaged with the implant, the abutment neck having an external concave surface that decreases in diameter in a direction from the proximal portion to the distal portion, the abutment neck defining an abutment cavity formed complementary to the external concave surface of the implant proximal segment to facilitate circumferential engagement; and a crown configured to be positioned over the abutment and the implant such that the crown covers the implant abutment joint, the crown having a crown distal portion defining a crown distal end having a crown cavity formed therein, and the crown cavity being configured complementary to at least a portion of the abutment proximal portion such that the crown distal end circumferentially engages the implant proximal segment.

15. The dental prosthesis of claim 14 wherein:

the proximal segment is defined by upper and lower conical surfaces;

the lower conical surface extending upwardly from a prosthetic margin and having a half angle of up to about 45 degrees;

the upper conical surface extending downwardly from the implant proximal end and having a half angle of up to about 5 degrees;

a radius being formed between the upper and lower conical surfaces.

16. The dental prosthesis of claim 15 wherein:

the implant distal segment has a height of about 1 mm;

the upper conical surface intersecting the radius at a tangent;

the external concave surface being configured such that the tangent is offset radially inwardly from the prosthetic margin by about 0.2 mm to about 1 mm.

* * * * *